United States Patent [19]

Shaffer

[11] Patent Number: 4,755,058

[45] Date of Patent: Jul. 5, 1988

[54] DEVICE AND METHOD FOR MEASURING LIGHT DIFFUSELY REFLECTED FROM A NONUNIFORM SPECIMEN

[75] Inventor: Gerald H. Shaffer, Wakarusa, Ind.

[73] Assignee: Miles Laboratories, Inc., Elkhart, Ind.

[21] Appl. No.: 866,730

[22] Filed: May 27, 1986

Related U.S. Application Data

[63] Continuation of Ser. No. 622,142, Jun. 19, 1984, abandoned.

[51] Int. Cl.⁴ ...................... G01N 21/31; G01N 21/47
[52] U.S. Cl. ..................................... 356/408; 356/446
[58] Field of Search .............................. 356/445–448, 356/408

[56] References Cited

U.S. PATENT DOCUMENTS

| 3,396,280 | 8/1968 | Knudsen | 356/445 |
| 3,473,878 | 10/1969 | Schweitzer | 356/446 |
| 3,604,815 | 9/1971 | Clemens | 356/448 X |
| 3,709,612 | 1/1973 | Clemens | 250/205 X |
| 3,907,503 | 9/1975 | Betts et al. | 356/446 X |
| 3,910,701 | 10/1975 | Henderson et al. | 356/73 X |
| 4,029,419 | 6/1977 | Schumann, Jr. et al. | 356/446 X |
| 4,029,420 | 6/1977 | Simms | 356/448 X |
| 4,218,144 | 8/1980 | Whitehouse et al. | 356/446 |
| 4,373,818 | 2/1983 | Yamamoto et al. | 356/408 |
| 4,518,259 | 5/1985 | Ward | 356/446 |
| 4,523,853 | 6/1985 | Rosenbladt et al. | 356/446 |
| 4,552,458 | 11/1985 | Lowne | 356/446 |
| 4,568,191 | 2/1986 | Barry | 356/446 |

OTHER PUBLICATIONS

O'Donovan et al, "Proximal Scanning Systems: Improved Resolution Using Inclined Optical Fibers", Applied Optics, vol. 15, #5, May 1976, pp. 1299–1303.

*Primary Examiner*—Vincent P. McGraw
*Attorney, Agent, or Firm*—Roger N. Coe

[57] ABSTRACT

A device for making accurate, reproducible light reflectance measurements on an optically nonuniform specimen comprises means for holding the specimen in a fixed position. In one embodiment the specimen is illuminated by light sources that are arranged at acute angles relative to the specimen and $(360°/N \pm 1°)$ apart in azimuth, where N=the total number of light sources. The light sources are sequentially energized and deenergized to illuminate the specimen. A light detector receives light reflecting from the surface and generates an electrical signal, which is subsequently processed. In another embodiment the light sources are arranged in pairs in which the two light sources in a pair are simultaneously energized and deenergized and the pairs are sequentially energized and deenergized. A method for measuring reflected light is also provided. The device and method are useful for making biochemical assays with reagent test strips by measuring the tone of coloration of the strips after treatment with a target substance being examined.

5 Claims, 3 Drawing Sheets

DEVICE AND METHOD FOR MEASURING LIGHT DIFFUSELY REFLECTED FROM A NONUNIFORM SPECIMEN

This is a continuation, of application Ser. No. 622,142, filed June 19, 1984, now abandoned.

BACKGROUND OF THE INVENTION

This invention relates to a method and a device for measuring light diffusely reflected from an optically nonuniform specimen, such as a reagent test strip used for qualitative and quantitative analysis of body fluids.

The spectral characteristics of light reflected by a specimen are related to the color of the specimen. With the advent of instrumental analysis, the color of a specimen under test has become one of the most widely used bases for biochemical assay procedures. For example, a reagent test strip used for qualitative and quantitative analysis can be contacted for a prescribed period of time with a body fluid, such as blood or urine. The reflectance spectrum of the colored test strip will vary depending on the concentration of the target substance in the body fluid being examined. Thus, by photoelectrically measuring light reflected from the test strip and computing the resulting reflectance, the desired analysis can be made by correlation of reflectance to concentration.

A reagent test strip is typically a test paper treated with various chemical reagents. Since the surface of the test strip does not have a uniform topography, it is difficult to make accurate and reproducible measurements because the result may depend on where the measurement is made on the strip or on measurement geometry. One solution to this problem has been to provide substantially uniform illumination of the test strip using an integrating sphere or hemisphere interposed between the light source and the strip. While this solution has met with some success, the integrating sphere or hemisphere adds to the cost of the device and may increase its size.

In addition, some illumination from the light source is dissipated or lost when an integrating sphere or hemisphere is utilized. Thus, in order to obtain a desired magnitude of reflected energy, the magnitude of the illumination must be correspondingly increased to compensate for the light dissipated in the device. This can require a larger light source and can lead to increased power consumption.

It has also been found with reagent test strips that the reflectance measurement is sensitive to the orientation of the strip in the test strip holder. For example, slight twisting or inclination of the specimen affects the magnitude of the reflectance measurement. In addition, it has been found that the reflectance measurement can be affected by the distance between the test strip and the light source.

Thus, there exists a need in the art for a method and a device for making rapid, accurate and reproducible light reflectance measurements from an optically nonuniform specimen under test. The device should employ direct illumination of the specimen to eliminate the need for an integrating sphere or hemisphere. The device should minimize the amount of illumination dissipated or lost between the light source and the specimen in order to minimize power consumption. The device should provide reflectance measurements that are less sensitive to subtle changes in the orientation of the specimen in the specimen holder and less susceptible to variations in the distance between the light source and the specimen. In addition, the device should be capable of compensating for changes in performance of components in the device, especially changes in illumination of the specimen.

SUMMARY OF THE INVENTION

Accordingly, this invention aids in fulfilling these needs in the art by providing a device for measuring light diffusely reflected from an optically nonuniform specimen. The device comprises means for holding an optically nonuniform specimen in a fixed position. At least two light source means provide direct illumination of the specimen in the form of incident beams of light that are coincident on a surface of the specimen. Means are provided for sequentially turning the light source means on and off for short periods in order to create pulses of incident light and pulses of reflected light. Light responsive means are provided for detecting light of substantially one wavelength from the resulting pulses of light reflecting from the surface. The light responsive means has an optical axis that is substantially perpendicular to the surface of the specimen. The light source means are about $(360°/N \pm 1°)$ apart in azimuth, where N equals the total number of light source means. Each light source means has a longitudinal axis that forms an acute angle with the surface.

This invention also provides a device for measuring light diffusely reflected from an optically nonuniform specimen comprising means for holding the specimen in a fixed position. First and second light source means provide direct illumination of the specimen in the form of two incident beams of light that are coincident on a surface of the specimen. Means are provided for simultaneously energizing and deenergizing each of the light source means to obtain the incident beams having substantially equal reflected energy and duration. Light responsive means detect light of substantially one wavelength from a beam reflecting from the surface. The light responsive means has an optical axis substantially perpendicular to the surface. The two light source means are about 179° to about 181° apart in azimuth and each light source means has a longitudinal axis that forms an acute angle with the surface; the acute angles are substantially equal.

In another embodiment, this invention provides a device for making accurate, reproducible light reflectance measurements on an optically nonuniform specimen. The device comprises means for holding the specimen in a fixed position. At least two pairs of light-producing means provide direct illumination of the specimen. Each pair comprises first and second light sources, and each light source in a pair is capable of projecting an incident beam of light coincident on a surface of the specimen. Means are provided for simultaneously energizing and deenergizing each of the light sources in a pair to obtain the incident beams having substantially equal reflected energy and duration and for sequentially energizing at least two of the pairs of light sources. Light responsive means detect light of substantially one wavelength from the light reflecting from the surface. The light responsive means has an optical axis substantially perpendicular to the surface. The light source means in each pair are about 179° to about 181° apart in azimuth. Each of the light sources in a pair has a longitudinal axis that forms an acute angle with the surface; the acute angles in a pair are substantially equal.

In a particularly preferred embodiment of this invention, the two light sources in each pair are capable of projecting a beam of substantially monochromatic light of the same wavelength on the surface of the specimen.

Further, this invention provides a method for measuring light diffusely reflected from an optically nonuniform specimen. The method comprises providing an optically nonuniform specimen in a fixed position and directly illuminating the specimen by projecting at least two incident beams of light from a corresponding number of light source means, wherein the beams are coincident on a surface of the specimen. At least two of the light source means are sequentially energized and deenergized to obtain the incident beams. Light of substantially one wavelength is detected from the beams reflecting from the surface at an angle substantially perpendicular to the surface. The light source means are about $(360°/N \pm 1°)$ apart in azimuth, where N equals the total number of light sources, and each of the light source means has a longitudinal axis that forms an acute angle with the surface.

This invention further provides a method for measuring light diffusely reflected from an optically nonuniform specimen by directly illuminating the specimen with two incident beams from first and second light source means and simultaneously energizing and deenergizing each of the light source means to obtain incident beams that are coincident on a surface of the specimen. Light of substantially one wavelength is detected from beams reflecting from the surface at an angle substantially perpendicular thereto. The two light source means are about 179° to about 181° apart in azimuth and form substantially equal acute angles with the surface.

In still another embodiment, this invention provides a method for measuring light diffusely reflected from an optically nonuniform specimen by directly illuminating the specimen by sequentially energizing and deenergizing two or more pairs of light-producing means, wherein each pair comprises first and second light sources capable of projecting two incident beams that fall coincident on a surface of the specimen. The light sources in a pair are simultaneously energized and deenergized to obtain the incident beams of substantially equal reflected energy and duration. Light of substantially one wavelength is detected by measuring beams reflecting from the surface at an angle substantially perpendicular to the surface. The light source means are about 179° to about 181° apart in azimuth. In a particularly preferred embodiment of this invention, the concentration or presence of a substance on a reagent test strip possibly bearing the substance is determined according to this method, wherein each light source in a pair is capable of providing substantially monochromatic light of the same wavelength.

BRIEF DESCRIPTION OF THE DRAWINGS

This invention will be more fully understood by reference to the drawings in which.

DETAILED DESCRIPTION

The device and method of this invention can be employed for measuring light diffusely reflected from an optically nonuniform specimen of essentially any type. As used herein, the expression "optically nonuniform specimen" means a specimen or a portion thereof that appears substantially flat to the unaided eye, but when a surface of the specimen is illuminated by a light source at a fixed elevation and spectral reflectance from the surface is measured, the mechanical nature of the surface is such that the reflectance measurement is a function of the azimuth angle. This definition can be more readily understood by reference to FIGS. 1 and 2 and the following descriptions of an optically uniform specimen and an optically nonuniform specimen.

Figure 1:
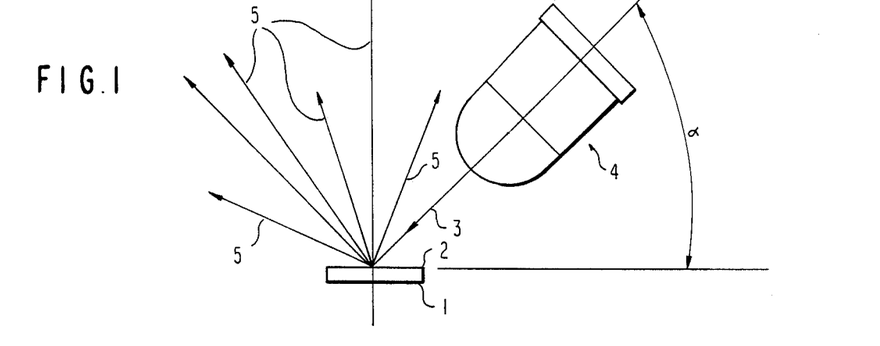
FIG. 1 is a cross-sectional view of a light source and specimen under test.

FIG. 1 shows a specimen 1 having a surface 2 illuminated by an incident beam of light 3 from a light source 4 which is at a fixed elevation with respect to the plane of surface 2. Light source 4 has a longitudinal axis that corresponds with the longitudinal axis of light beam 3. The angle of incidence of the light source 4 with respect to the surface 2 is identified as $\alpha$. The incident beam 4 is scattered from the surface 2 as diffusely reflected energy 5.

Figure 2:
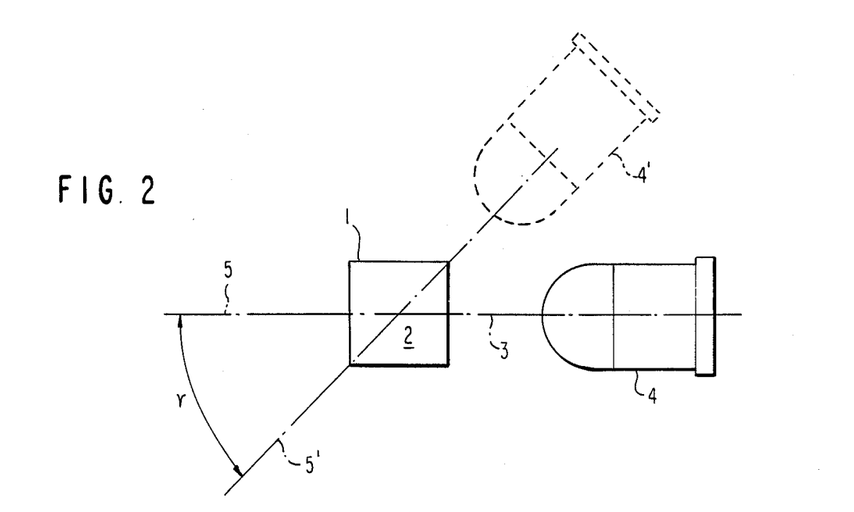
FIG. 2 is a plan view of the light source and specimen shown in FIG. 1.

FIG. 2 is a top view of the arrangement shown in FIG. 1. The incident beam of light 3 from illumination source 4 reflects from surface 2 as reflected beam 5. In the case of an optically nonuniform specimen, the spectral reflectance produced by source 4 at a fixed angle of incidence will change if the light source 4 is moved from the position shown in solid lines in FIG. 2 to the position shown in phantom in FIG. 2. This change in position is defined by the azimuth angle $\gamma$ and thus, in the case of an optically nonuniform specimen, the spectral reflectance is a function of the azimuth angle. In the case of an optically uniform specimen, however, the spectral reflectance is unaffected by movement of the light source 4 to the position shown in phantom, provided that, in each position the source 4 is at the same angle of incidence ($\alpha$) to the surface 2.

The device and method of this invention will now be described in connection with the measurement of reflectance from a reagent test strip for purposes of color identification.

Figure 3:
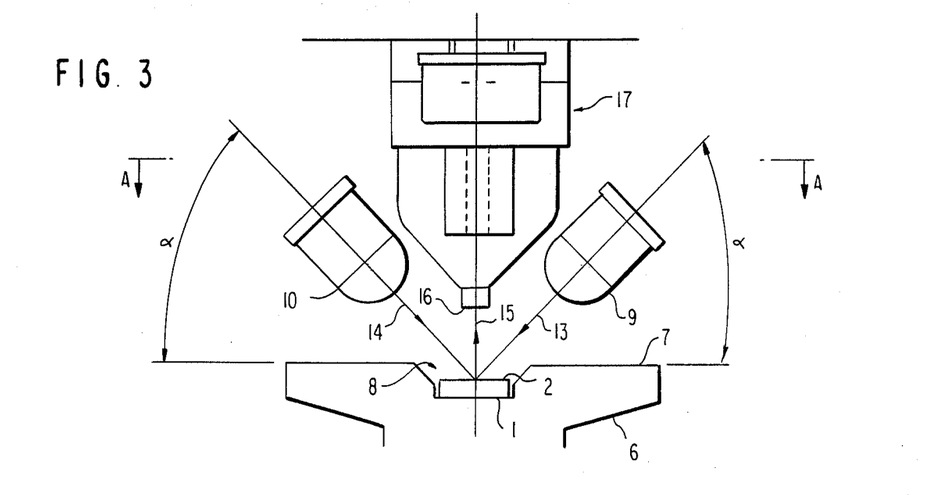
FIG. 3 is a sectional view of a reflectance measuring device of this invention.

One embodiment of a reflectance measuring device of this invention is shown in FIG. 3. The device comprises a work holder 6 having a planar surface 7 with a recess 8 for supporting a specimen 1 under test. The device includes two diffuse light sources 9 and 10 for substantially uniformly illuminating the top surface 2 of specimen 1. Light source 9 projects a beam 13 of monochromatic light having a longitudinal axis that coincides with the optical axis of the light source. In the same fashion, light source 10 projects a beam 14 of monochromatic light of the same wavelength as beam 13 unto the surface 2. Light source 9 and light source 10 are held in a fixed position and each light source makes substantially the same angle ($\alpha$) with the surface 2 of specimen 1 so that substantially equal incident angles of light on the surface under test are obtained. Since the light sources are at the same elevation angle, the beams from both sources are substantially coincident on surface 2.

Components of each beam reflect perpendicularly upward from the surface 2 and combine to form reflected beam 15 having a magnitude that is a function of the degree of coloration of the surface under test. The reflected beam 15 enters a sensing head 16 of light detector 17. The light detector 17 is usually a photodetector having an optical axis (not shown) coincident with the longitudinal axis of reflected beam 15 and the coincident axes are normal to the top surface 2.

Figure 4:
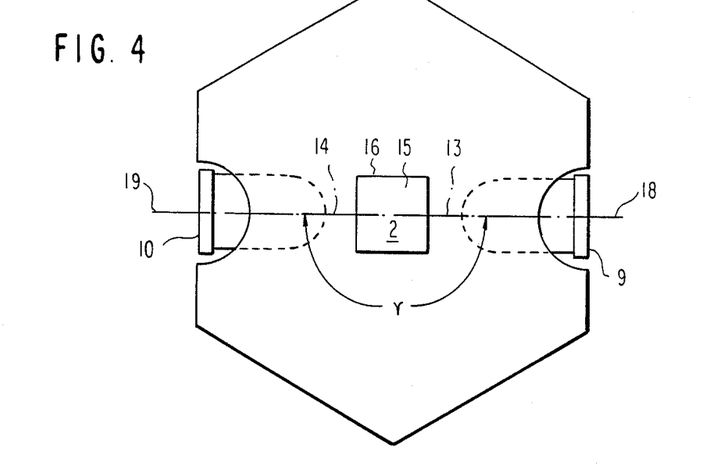
FIG. 4 is a plan view of the reflectance measuring device through section A—A in FIG. 3.

Referring to FIG. 4, it will be seen that light source 9 and light source 10 are 180° apart in azimuth. The azimuth angle is shown as the angle $\gamma$, which is formed by the angle between the optical axes 18 and 19 of the light sources 9 and 10, respectively.

The device is operated by holding specimen 1 in a fixed position while the light sources are simultaneously and sequentially energized and deenergized for periods of very short duration in order to create short pulses of light that illuminate surface 2. As the light sources are pulsed on and off, the pulsed, reflected energy 15 is measured with photodetector 17. The reflected energy 15 is then converted to electric signals and electronically processed in a logic system having a comparator circuit for comparing the signals with a reference level and for converting the result to the desired parameter, such as the concentration of a protein in a blood sample under test. It has been found that very accurate and reproducible reflectance measurements can be made on an optically nonuniform specimen with this device and the procedure described. The reflectance measurement is less sensitive to slight changes in the orientation of the specimen in the specimen holder. In addition, it is not necessary to use a light diffusing apparatus between the light source and the specimen. It has also been found that the reflectance measurement is less susceptible to slight changes in the distance between the specimen and the light source.

Figure 5:
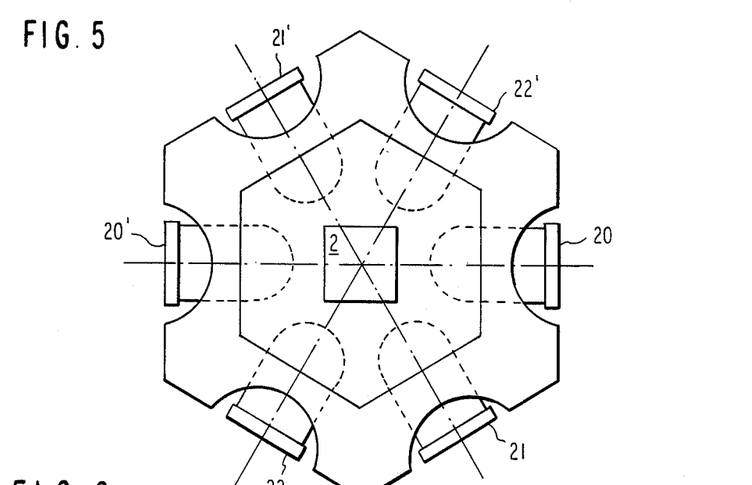
FIG. 5 is a plan view of a preferred reflectance measuring device of this invention having multiple pairs of light sources.

Another embodiment of this invention is shown in FIG. 5, which depicts a device incorporating a multiplicity of light sources. In this embodiment the surface 2 of specimen 1 is illuminated by N light sources, where N=6. The light sources are designated 20, 21, 22, 20′, 21′ and 22′. It is apparent from FIG. 5 that the six light sources are arranged 360°/N apart in azimuth. The light sources are at substantially the same angle of incidence ($\alpha$, as in FIG. 3) with respect to the top surface 2. It is not necessary that all of the light sources provide the same wavelength of light.

Each of the light sources in FIG. 5 is energized and deenergized in sequence so that the surface 2 of specimen 1 is periodically illuminated by pulses of light from the sources. The resulting pulses of reflected light 15 are collected by photodetector 17 (see FIG. 3) where they are converted to electrical signals. The signals are processed, and the reflectance from the optically nonuniform specimen is computed.

The device shown in FIG. 5 can be converted to a preferred embodiment of this invention as follows. In the preferred embodiment the surface 2 of specimen 1 is illuminated by opposing light sources that are arranged in pairs designated 20—20′, 21—21′ and 22—22′. It is apparent from FIG. 5 that the two light sources in each pair are arranged 180° apart in azimuth. In addition, the two light sources in each pair are at substantially the same angle of incidence ($\alpha$, as in FIG. 3) with respect to the top surface 2. The two light sources in each pair are capable of providing a beam of monochromatic light of the same wavelength, but all of the light source pairs need not provide the same wavelength of light. Thus, for example, while the light beams from light sources 20 and 20′ each have the same wavelength, this wavelength need not be the same as the wavelength of the light beams provided by sources 21 and 21′. Similarly, light sources 22 and 22′ provide light beams of the same wavelength, but this wavelength need not be the same as the wavelength provided by light sources 20 and 20′ or 21 and 21′.

In the preferred embodiment, the two light sources in each pair are simultaneously energized and deenergized and each pair of light sources in FIG. 5 is energized and deenergized in sequence so that the surface 2 of specimen 1 is periodically illuminated by pulses of light from the two sources in each pair. The resulting pulses of reflected light 15 are once again collected by photodetector 17 (see FIG. 3) where they are converted to electrical signals. The signals are processed, and the reflectance from the optically nonuniform specimen is computed.

The various components in the apparatus of this invention will now be described in more detail.

The device of this invention contains N light sources, where N is two or more. The upper limit to the number of light sources is generally not critical in practicing this invention. Nevertheless, the number of light sources may be limited by practical considerations, such as cost and physical constraints. Generally, the number of light sources will not exceed about 200. When a large number of light sources is employed, it may be necessary to space some or all of the sources at a distance from the specimen and to use light focussing means or a light guiding arrangement, such as fiber optics, to transmit the light from the source to the specimen. Up to about twenty light sources, for example ten pairs, can typically be spaced close enough together without providing light guiding means. While the number of light sources and the geometry of the placement of pairs of light sources around the specimen can be adapted to each application, in the preferred embodiment of this invention, six light sources (three pairs) are symmetrically arranged and substantially uniformly spaced around the specimen (see FIG. 5).

The angle ($\alpha$) of incident light on the surface of the specimen under test can be varied depending upon the nature of the specimen, the nature of the light sources, the nature of the detector and related circuitry for processing the signal from the detector and the degree of accuracy required in the measurement. If the incident angle is too great, specular reflection collected by the photodetector will be too high, thus making it difficult or impossible to resolve the signal from the detector into the diffusely reflected components that will indicate the tone of coloration. If the elevation angle is too low, insufficient illumination will be collected by the detector and the signal from the detector may be too low or unreliable. It has been found that the angle of elevation can be about 40° to about 50° when measurements are made on reagent test strips. Preferably, the angle of incident light will be about 44° to about 46° for reagent test strips, which is generally adequate to allow for manufacturing tolerances in the device. In the particularly preferred embodiment of this invention, the longitudinal axis of each light source forms an angle ($\alpha$) of substantially 45° with the surface 2. When the light sources are employed in pairs, the incident light from each of the two light sources in a light source pair makes substantially the same angle with the surface of the specimen, but small deviations in these angles within the foregoing ranges can be tolerated.

When the light sources are employed in pairs, not all of the pairs of light sources need to be at the same incident angle relative to the surface under test. For example, the incident angle of each of the two light sources in one pair could be about 44° and the incident angle of each of the two light sources in another pair about 46°. This arrangement may make it possible to space the light sources closer together and thereby employ more light source pairs in the device.

Since the light sources are at an inclined angle relative to the surface under test, elliptical illumination patterns are formed. If the incident beams from the light sources are focussed on a small, concentrated spot on the surface, the detector will have to be carefully aimed at the spot and the acceptable tolerance in deviation in incident angles will be small. For these reasons, and because low cost, commercially available light sources produce broad illumination patterns, it has been found advantageous to illuminate a large area of the surface and to focus the detector on a small portion of this area. In the preferred embodiment, the complete reagent area of a reagent test strip is illuminated and the detector is focussed on a small portion of the area by placing apertures between the surface and the detector.

When pairs of light sources are employed, each light source in a pair projects light onto the surface 2 of specimen 1. Under ideal conditions, the two illumination patterns are superimposed to form a homogeneous pattern of light and a homogeneous reflected beam 15.

The azimuth angle can be varied depending upon the number of light sources (i.e., N) and the degree of accuracy required in the measurement. In one embodiment of the invention the light sources are arranged about 360°/N apart in azimuth. Thus, for example, 6 light sources are arranged about 60° apart, 5 light sources about 72° apart, 4 light sources about 90° apart and 3 light sources about 120° apart. When making reflectance measurements on reagent test strips, deviations in azimuth angles of ±1° are generally acceptable, and these deviations are usually sufficient to allow for manufacturing tolerances in the device. Thus, the azimuth angle can be conveniently expressed as (360°/N±1°).

When the light sources are employed in pairs as described with reference to FIG. 5, the azimuth angle can be varied depending upon the degree of accuracy required in the measurement. If the azimuth angle deviates from 180°, the illumination patterns will not be superimposed, and in the extreme case, two separate illumination spots can form. The detector 17 receives energy from only a small area of the surface of the specimen. Thus, if the illumination patterns diverge from a homogeneous spot of light, a false reflectance reading can result. This could occur, for example, if there was a dark area between the diverging patterns or if the detector collected more of the reflected light from one source than from the other. When making reflectance measurements on reagent test strips, the azimuth angle between the two light sources in a pair can generally be between about 179° to about 181°, which is generally sufficient to allow for manufacturing tolerances in the device. In the preferred embodiment of this invention, the azimuth angle between light sources in a pair is about 180° in order to maximize the accuracy of the reflectance measurement.

In the preferred embodiment, the light source is capable of producing a reflected beam of monochromatic light in the region of the electromagnetic spectrum to which the specimen and the detector respond. While the light sources can be selected so that they all produce reflected light of the same wavelength, it is only required that the the reflected beam from the two light sources in each light source pair be of substantially one wavelength. Light in the visible region of the spectrum is generally employed; this light is especially well suited for measuring reagent test strips. Typically, the light source will be capable of emitting light having a wavelength of about 550 nanometers (nm) to about 940 nm, preferably about 550 nm to about 660 nm. In the embodiment depicted in FIG. 5, the three pairs of light sources emit light having wavelengths of about 557 nm, about 610 nm and about 660 nm, respectively.

The use of light-emitting semiconductor devices, such as light-emitting diodes (LEDs), has been found to be particularly advantageous in this invention. Light-emitting diodes capable of emitting diffuse, monochromatic light are commercially available in the wavelength ranges previously described. The light-emitting diodes are of low cost, have low power requirements and high radiance and can be directly modulated at high rates. In addition, they are typically available in small sizes, which makes it possible to arrange multiple pairs of LEDs around the work holder without the use of light guiding means, such as fiber optic bundles. Exemplary LEDs are those based on GaAlAs, GaP, GaAsP/GaP and equivalent chip materials. In the preferred embodiment depicted in FIG. 5, monochromatic illumination is provided by six high efficiency light-emitting diodes of the Stanley ESAA-, ESBR- and ESBG-5531 Series available from Stanley Electric Co., Ltd.

The light source can also consist essentially of polychromatic light and means for separating all but the light of substantially one wavelength so that monochromatic light is emitted from the source. This can typically be accomplished with a tungsten lamp and a suitable filter interposed between the lamp and the surface of the specimen under test.

The specimen is held in a fixed position while reflectance is being measured, but can be moved to permit scanning of the surface or the measurement of reflectance from a different area of the specimen.

It is important that the output from each light source be stable in order to obtain accurate and reliable reflectance measurements because changes in output of the light source are indistinguishable to the detector from changes in reflected energy from the specimen. In some cases, it is even necessary to make several readings over the surface of the specimen, and in this event, it is also important that the output of each light source be stable while each reading is being taken. For example, a reagent test strip is frequently provided with several different reagents for making several different biochemical assays at one time, and it is important that the output from each light source be stable while the color of each reagent is being determined. By energizing and deenergizing the pairs of light sources so that the light sources in a pair are turned on and off at the same time, light pulses are generated. Stable, reproducible output from each light source can be obtained by pulsing the sources in this way.

The light pulses are generated by feeding to the light sources pulses of electric current having a duration sufficient to obtain the stable, reproducible output. The duration of each pulse will depend upon the nature and operating characteristics of the source and the speed of response of other components of the device. Pulsing can be accomplished by switching and timing means operable such that a selected light source or any combination of selected pairs of light sources are energized and deenergized. For instance, stable output can generally be obtained with LEDs energized for about 100 to about 300 milliseconds at about 20 to about 25 milliamps input current. At higher input currents, heat is generated in the light source and the heat may adversely affect the stability and reproducibility of the output. In order to minimize the adverse affects of the heat, the duration of energization of the light source will typically be reduced at the higher input currents. The duration of the on-off cycles for the light sources in a pair will be substantially equal.

When pairs of light sources are employed, all of the pairs of light sources can be pulsed at the same time or selected pairs can be pulsed in sequence. For example, light source pairs of the same wavelength can be pulsed simultaneously or in sequence. On the other hand, light source pairs of different wavelengths will generally only be sequentially pulsed because of the difficulty in separating the reflected beam (15 in FIG. 3) into monochromatic components at the detector. The order in which the pairs of light sources are pulsed has not been found to be critical.

Figure 6:
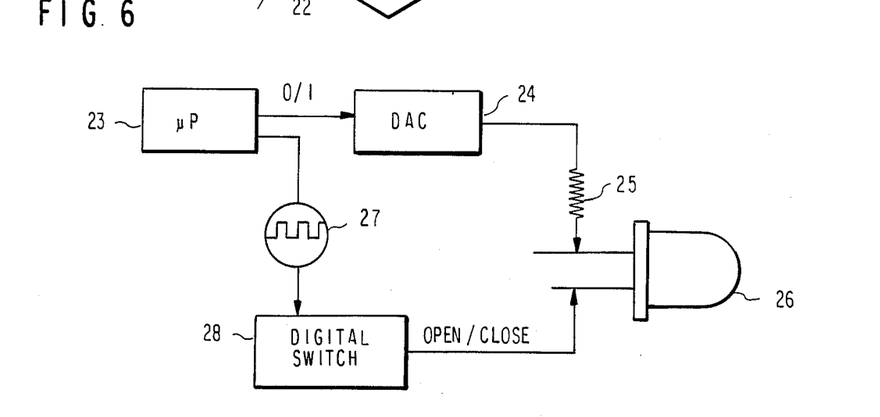
FIG. 6 is a schematic diagram of apparatus for controlling light sources employed in this invention.

FIG. 6 is a schematic diagram of an apparatus for controlling the on-off cycle and output of each light source by means of a microprocessor ($\mu P$) 23. Digital signals (0/1) are sent through a digital to analog converter (DAC) 24, the output 25 of which powers the light source 26. The microprocessor 23 also controls a timer 27 connected to digital switch 28, which opens and closes to turn the light source on and off for the required duration. The resulting pulses of light should be of sufficient duration for the electronic and optical components of the device to respond, but not so long that variations caused by instability in the light sources adversely affect the accuracy of measurement. Each light source can be pulsed more than one time, if desired, and the pulse cycle can be repeated as needed.

The duration of the pulse of electric current can be varied over a wide range. For example, the light sources of a particular wavelength may have low output or the detector may not have the same sensitivity to each of the different wavelengths of reflected light being measured. Thus, for example, the duration of the pulses to the light sources in one pair can be different than the duration of pulses to the light sources in another pair of different wavelength.

The intensities of the light beams from the light sources can also be varied over a wide range. Ordinarily, the desired magnitude of the energy reflected from the specimen will be established based upon the sensitivity of the detector and nature of the circuitry for processing the signal from the detector. The intensities of the light beams should be adequate to provide a reflected beam of at least the desired magnitude under the test conditions so that it is possible to discriminate between changes in color in the specimen. The intensity of each light beam can be controlled by regulating input current to the source. The input current will vary depending on the nature of the light source and its operating characteristics. For example, in the preferred embodiment shown in FIG. 5, each light source is an LED energized by a 20 milliamp input current. The light sources having a 557 nm wavelength produce a 12 to 18 millicandela (mcd) output, the light sources having 610 nm wavelength produce a 20 to 30 mcd output and the light sources having a 660 nm wavelength produce a 32 to 48 mcd output when reagent test strips are being measured. Thus, it will be evident that the intensity of the incident beams can vary from one light source pair to another, such as where the pairs produce monochromatic light of different wavelengths.

The output from each light source must not only be stable, but the contribution of each of the two light sources in a pair of light sources to the total reflected energy must be substantially equal to insure accurate, reproducible measurements. When measuring reagent test strips, the difference between LEDs of a pair should typically be within about ±2.5%. Because the output of commercially available light sources can vary by as much as ±50% and because the output of each source can change depending upon varying rates of degradation, means can be included in the device for periodically measuring the reflected energy due to each source and then increasing or decreasing the input to the source as needed to obtain the desired level. Acceptable matching of the light sources can be achieved by measuring the energy from each source that is reflected by the specimen under test and then making the appropriate adjustment to the input. Light source output fluctuations could be monitored by placing a reference detector such that it intercepts a portion of the beam from the light source and provides appropriate feedback to vary the input, but this requires a reference detector for each source. A simpler method is shown in FIG. 7.

Figure 7:
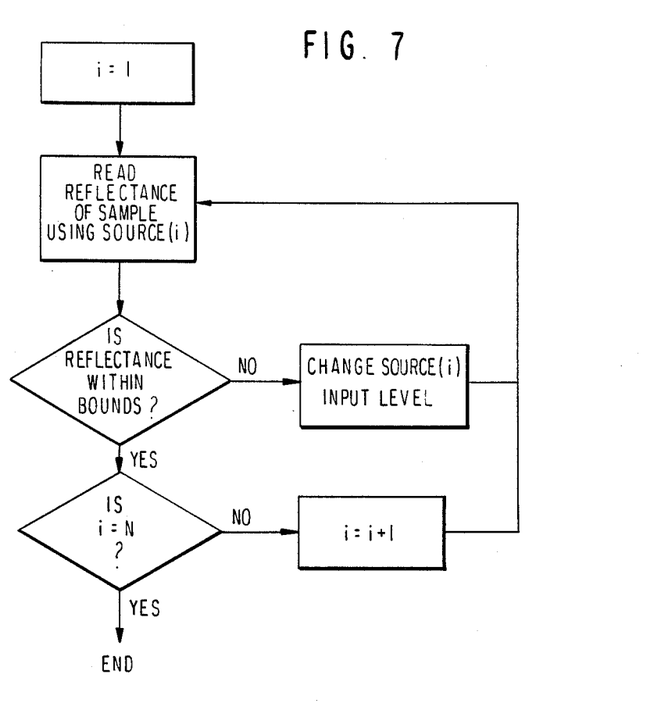
FIG. 7 is a logic diagram of means for equalizing the output from light sources in the device of the invention.

With reference to FIG. 7, N is the total number of light sources in the device of the invention. The letter "i" is the program counter. Beginning with i=1, i.e., the first light source, each source, in sequence, illuminates a specimen and the reflected energy is read by the single detector 17 (see FIG. 3). The reflectance associated with each source is compared to a preset window of values and the input to each source adjusted accordingly to increase or decrease light output. The procedure is repeated for the second light source (i=2), the third light source (i=3), and so on, for i=N light sources. This procedure can be readily carried out by including in the device a solid state logic circuit that can be readily designed by one skilled in the art and a conventional controller for regulating the input to each light source. Precision is increased by using a single detector in this way for all reflectance measurements, because the variation in responsivity of detectors is small compared to variation in output among light sources. This increase in precision is achieved at no additional cost and without an increase in the size of the device.

Another advantage of this embodiment is that in matching reflected energy, compensation is made for all components in the optical path, not only the light source, which might preferentially affect output of one or more light sources.

In addition, sensitivty of the reflectance measurement to twisting or inclination of the specimen is minimized by matching the reflected energy due to each source.

For instance, with a single light source, rotation or inclination of the specimen will result in an increase or decrease in the total reflected energy reaching the detector, depending upon the direction of movement relative to the detector. Because this change in reflected energy has no relation to the color of the specimen, the rotation introduces an error in the reflectance measurement. A similar error is introduced if a pair of light sources is employed and the contribution of one light source to the total reflected energy is much greater than the other light source. If, however, both light sources in the pair contribute essentially equal amounts of reflected energy, as the sample rotates, the contribution from one light source decreases and the contribution from the other source proportionally increases so that the total energy received by the detector is essentially constant. Thus, it is important to match the contribution of each light source to the total reflected energy received by the detector since only reflected energy takes the sample characteristics into account.

Still other advantages in matching reflected energy of the light sources in a light source pair is that sensitivity to variations in the distance between the light source and specimen is minimized and matching the light sources produces an averaging effect; any characteristic of the light sources is averaged by employing multiple, matched light sources. For example, if the prescribed wavelength for a pair of light sources is 557 nm, but one source actually operates at 560 nm and the other at 554 nm, the average wavelength of reflected energy will be 557 nm if the light sources are balanced so that each source makes an equal contribution to the total reflected energy. If the light sources are not balanced, then the wavelength of the reflected energy will be biased toward the wavelength of the brighter source.

The photodetector is selected so that it will respond over the range of wavelengths of light reflecting from the specimen or emitted by the light sources and reflected by the sample under the test conditions. The photodetector should have high sensitivity to the light and fast enough response time to accommodate the data rate being used. In the preferred device of this invention, the photodetector is responsive to light having wavelengths in the range of about 500 to about 700 nm at about 25° C. The photodetector is preferably a silicon photodiode operated in the photovoltaic mode.

The light detector is fixed in a position so that its optical axis substantially coincides with the longitudinal axis of the reflected beam. This will ensure efficient collection of the reflected beam by the detector. The detector will generally be placed in close proximity to the surface of the specimen under test in order to minimize transmission losses as the reflected beam travels between the specimen and the detector. In some cases, however, such as where space is limited, the detector can be spaced farther away from the specimen by selecting a detector having a larger viewing area or by incorporating light guiding means between the specimen and detector. The detector can be moved to permit scanning of the surface under test or for the measurement of reflectance from a different area of the specimen. Similarly, movement of the detector can be coordinated with movement of the specimen.

While the preferred embodiment of the invention has been described in terms of a light source capable of producing monochromatic light, it will be understood that the invention can also be practiced with a light source capable of producing polychromatic light and means for separating all but the light of substantially one wavelength from the reflected beam (15 in FIG. 3) so that diffuse monochromatic light having the characteristics previously described activates the detector or is received in the detector. This can be accomplished, for example, by employing a monochromatic detector or by interposing a suitable optical filter in the path of the reflected beam between the specimen and the detector.

Figure 8:
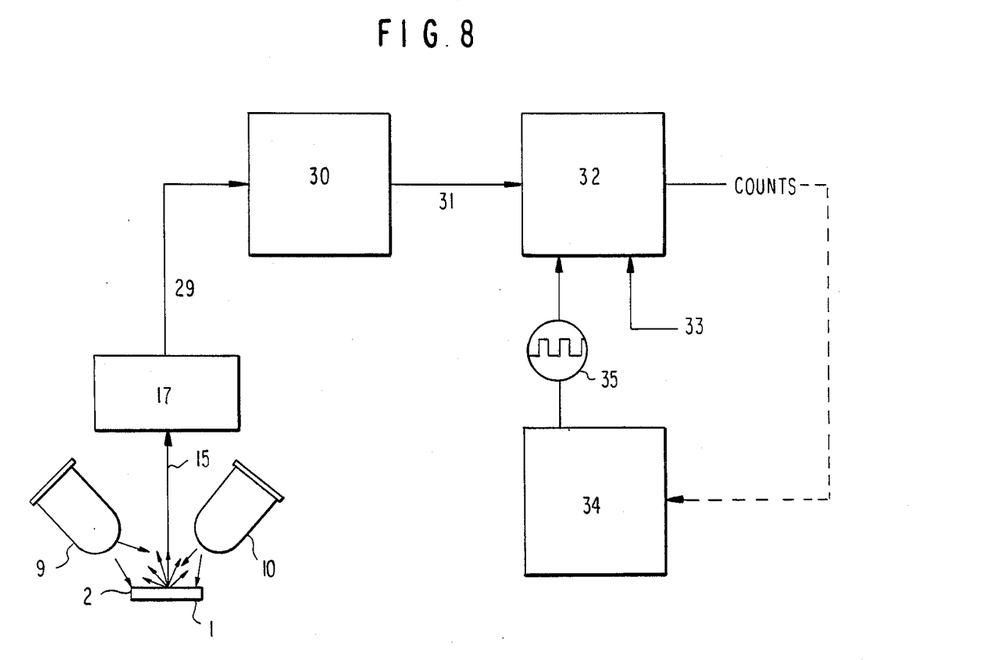
FIG. 8 is a schematic diagram of apparatus for processing a signal from a detector in the device of this invention.

Processing of the signal will now be described with reference to FIG. 8 depicting apparatus employed with the preferred silicon photodiode detector operated in the photovoltaic mode. Light sources 9 and 10 directly illuminate the surface 2 of specimen 1, and reflected beam 15 is collected by photodiode 17. The photodiode 17 produces a current 29 that is fed to an operational amplifier 30 used as a high gain current to voltage converter. The photodiode 17 and operational amplifier 30 are connected such that higher levels of illumination produce less positive voltage levels.

Analog to digital conversion of voltage output 31 from the operational amplifier 30 is accomplished in analog to digital converter 32 by a dual ramp integration technique. The signal voltage 31 is applied to an integrator for a time period that is a fixed number of microprocessor clock cycles—50 milliseconds (msec) in the preferred embodiment. This is achieved via microprocessor 34 and timer 35. A reference voltage 33 of opposite polarity is then applied. Clock cycles are counted until the integrator voltage drops below a threshold as detected by a comparator (not shown). When this time interval is ratioed to the fixed integration time, the value obtained represents the proportion of signal to the reference and the value is termed "counts." An offset value is first measured by reading "counts" with no illumination on the specimen 1. With the light sources 9 and 10 turned on, "counts" are first read from a standard specimen of known reflectance and second, from the unknown specimen. Reflectance is then calculated in microprocessor 34 from the following formula:

$$\frac{\text{COUNTS(unknown)} - \text{COUNTS(offset)}}{\text{COUNTS(standard)} - \text{COUNTS(offset)}} \times$$

Reflectance of Standard

The calculated reflectance value can then be compared with reflectance values for specimens of known color and the desired analysis displayed in a permanent or transient state.

When multiple light source pairs are employed for making reflectance measurements, not all of the pairs need to be energized for all types of specimens. For example, only one or two of the light source pairs in FIG. 5 may be energized and reflectance measurements based on the resulting signals generated. If all of the pairs are sequentially energized and reflectance measured for all the pairs, not all of the resulting measurements need to be employed in the analysis. This permits wide flexibility in programming the device of this invention to make measurements on specimens of different types, such as specimens that respond to only some of the wavelengths of light emanating from the light sources.

The device of this invention is capable of making very accurate and reproducible light reflectance measurements on optically nonuniform specimens. Thus, the device and method of this invention can be used to measure the concentration or presence of a substance on a reagent test strip by determining the tone of coloration by instrumental analysis. It will be apparent from the foregoing discussion and the Figures that the surface of the specimen is lighted by substantially uniform, direct illumination; that is, there is no diffusion apparatus or mechanism between the light source and the specimen. Thus, it is not necessary to obtain perfectly diffuse illumination of the surface under observation to obtain accurate analyses. The specimen can be illuminated at lower cost and with smaller size by elimination of an integrating sphere or hemisphere and by greater magnitude of illumination for equivalent sources. The amount of illumination lost between the light source and specimen and the amount of power consumed are minimized. In addition, slight variations in the orientation of the specimen in the specimen holder and in the distance between the light source and specimen can be tolerated.

What is claimed is:

1. A device for measuring light diffusely reflected from an optically nonuniform specimen, said device comprising:

means for holding an optically nonuniform specimen in a fixed position;

first and second light source means for providing direct illumination of said specimen in the form of two incident beams of light that are coincident on a surface of said specimen;

means for simultaneously energizing said light source means for periods not exceeding about 300 milliseconds at an input current of about 20 to about 25 milliamps and then deenergizing each of said light source means to obtain said incident beams having substantially equal reflected energy and duration, the difference in the reflected energy of said incident beams being within ±2.5%;

light responsive means for detecting light of substantially one wavelength in the range of from about 550 to about 940 nanometers from said beams reflecting from said surface, said light responsive means having an optical axis substantially perpendicular to said surface;

said two light source means being about 179° to about 181° apart in azimuth and each of said light source means having a longitudinal axis that forms an acute angle with said surface, wherein each acute angle is substantially equal;

wherein said light responsive means for detecting light produces an electrical signal in response to the energization and deenergization of each of said light source means;

means for comparing said electrical signal with corresponding values of a specimen of known reflectance and computing the reflectance from said optically nonuniform specimen; and means for reporting the resulting computed reflectance.

2. The device of claim 1 wherein said acute angles are about 40° to about 50°.

3. The device according to claim 1 wherein said acute angles are about 44° to about 46°.

4. A method for measuring light diffusely reflected from an optically nonuniform specimen, said method comprising:

providing an optically nonuniform specimen in a fixed position;

directly illuminating said specimen by projecting at least two incident beams of light from a corresponding number of light source means, wherein said beams are coincident on a surface of said specimen, said light source means being about $(360°/N \pm 1°)$ apart in azimuth, where N equals the total number of light source means, and each of said light source means has a longitudinal axis that forms an acute angle with said surface;

sequentially energizing for periods not exceeding about 300 milliseconds at an input current of about 20 to about 25 milliamps and then deenergizing at least two of said light source means in order to create pulses of incident light and pulses of reflected light having substantially equal reflected energy and duration, the difference in the reflected energy of said incident beams being within ±2.5%;

detecting light of substantially one wavelength within the range of about 550 to about 940 nanometers from said pulses of light reflecting form said surface at an angle substantially perpendicular to said surface;

producing an electrical signal from said detected light in reponse to said pulses of reflected light;

comparing said electrical signal with corresponding values of a specimen of known reflectance;

computing the reflectance from said optically nonuniform specimen; and reporting said computed reflectance.

5. The method according to claim 4 wherein N is an even number between 2 and 20.

* * * * *